US012709496B2

(12) United States Patent
Owston

(10) Patent No.: US 12,709,496 B2
(45) Date of Patent: Aug. 18, 2026

(54) SYSTEM AND METHOD FOR A WORKING MACHINE

(71) Applicant: J. C. Bamford Excavators Limited, Rocester (GB)

(72) Inventor: Edward Owston, Uttoxeter (GB)

(73) Assignee: J.C. Bamford Excavators Limited, Uttoxeter (GB)

( * ) Notice: Subject to any disclaimer, the term of this patent is extended or adjusted under 35 U.S.C. 154(b) by 393 days.

(21) Appl. No.: 18/102,677

(22) Filed: Jan. 27, 2023

(65) Prior Publication Data

US 2023/0264905 A1 Aug. 24, 2023

(30) Foreign Application Priority Data

Feb. 2, 2022 (GB) ...................................... 2201347

(51) Int. Cl.
*B65G 65/00* (2006.01)
*B65G 3/04* (2006.01)
(Continued)

(52) U.S. Cl.
CPC ............. *B65G 65/005* (2013.01); *B65G 3/04* (2013.01); *B65G 65/04* (2013.01); *G01N 33/025* (2013.01)

(58) Field of Classification Search
CPC ........ B65G 65/005; B65G 3/04; B65G 35/04; A01F 25/18; A01F 25/183; A01F 25/166; A01F 25/186
See application file for complete search history.

(56) References Cited

U.S. PATENT DOCUMENTS 5,850,341 A * 12/1998 Fournier ............... E02F 9/2045 701/34.2
6,671,698 B2 * 12/2003 Pickett ................. G06Q 10/087 705/37

(Continued)

FOREIGN PATENT DOCUMENTS

DE 102016224294 A1 6/2018
GB 2487435 A 7/2012

OTHER PUBLICATIONS

Extended European Search Report issued in EP 23 15 4585, dated Jun. 22, 2023.

(Continued)

*Primary Examiner* — Patrick H Mackey
(74) *Attorney, Agent, or Firm* — MARSHALL, GERSTEIN & BORUN LLP

(57) ABSTRACT

A system for mapping one or more characteristics of a body of a harvested crop stored in a storage space includes a controller; a first device assembly providing an input to the controller; and a second device assembly providing an input to the controller. The controller is configured to determine one or more characteristics of each of a plurality of portions of the body of the harvested crop, such as dry matter content, moisture content, level of contamination, and/or one or more nutrient values, prior to the deposition of each of said portions in the storage space based on at least the input from the first device assembly. The controller is configured to determine a location at which each of said portions is deposited in the storage space based on at least the input from the second device assembly. The controller is configured to store the determined one or more characteristics and the determined location of each of said portions in a database.

19 Claims, 10 Drawing Sheets

(51) Int. Cl.
*B65G 65/04* (2006.01)
*G01N 33/02* (2006.01)

(56) References Cited

U.S. PATENT DOCUMENTS

| | | | | |
|---|---|---|---|---|
| 7,996,134 | B2 * | 8/2011 | Roberts | G01S 19/13 701/50 |
| 9,014,924 | B2 * | 4/2015 | Edara | E02F 9/205 701/50 |
| 2003/0182144 | A1 | 9/2003 | Pickett et al. | |
| 2007/0150147 | A1 * | 6/2007 | Rasmussen | E01C 19/004 701/50 |
| 2008/0266175 | A1 | 10/2008 | Roberts | |
| 2010/0159114 | A1 * | 6/2010 | Yager | A01F 25/166 426/636 |
| 2011/0320033 | A1 * | 12/2011 | Bresciani | A01K 5/0275 700/213 |
| 2012/0029815 | A1 * | 2/2012 | Roberts | G01S 19/13 701/400 |
| 2014/0095032 | A1 * | 4/2014 | Mulder | G01G 13/02 701/50 |
| 2018/0332760 | A1 | 11/2018 | Gresch et al. | |
| 2020/0068023 | A1 * | 2/2020 | Nygren | B62D 49/02 |
| 2021/0321571 | A1 * | 10/2021 | Brocke | A01F 25/183 |
| 2021/0329844 | A1 * | 10/2021 | Brocke | A01F 25/183 |

OTHER PUBLICATIONS

Search Report issued in GB Patent Application No. 2201347.8, dated Mar. 17, 2022.

* cited by examiner

| | Harvesting Location | Harvesting Time | Moisture | Dry Matter | Sugar Content | ... | |
|---|---|---|---|---|---|---|---|
| 1 | | | | | | | |
| 2 | | | | | | | |
| 3 | | | | | | | |
| 4 | | | | | | | |
| ⋮ | | | | | | | |
| N | | | | | | | |

SYSTEM AND METHOD FOR A WORKING MACHINE

FIELD

The present teachings relate to a system and method for mapping one or more characteristics of a body of a harvested crop stored in a storage space, a working machine, and an attachment for mounting to a working arm of a working machine.

BACKGROUND

Silage is a foodstuff for cattle that is most commonly made from grass and maize, but may also be made from alfalfa, vetches, oats, rye or sorghum. It is an effective way of storing these crops from a harvest time in summer months for animal feed in winter when such crops are not available, whilst preserving their nutritional content. Silage is made by compacting the crop to minimize the volume it takes up and to expel air, before enclosing it in an impermeable enclosure and allowing it to ferment over several weeks in this anaerobic environment. The enclosure is then opened and the silage is fed to livestock as required.

One way of forming the impermeable enclosure is to wrap a bale of the crop in plastics sheeting. Another way to form the impermeable enclosure is to deposit a large amount of the crop in a clamp or pit with a base and three walls forming an incomplete rectangle and then covering the exposed surface of the crop in a plastics sheet.

Working machines, specifically material handling machines, of various types such as wheeled loading shovels, telescopic handlers, tractors and the like have traditionally been used in depositing the harvested crop in the clamp and the compaction of harvested crop to form silage. Typically, the working machine passes over the harvested crop, and the weight of the working machine compacts the crop via the wheels. The working machine has a working arm, and an attachment to the working arm, such as forks or a push-off buckrake, which is used to distribute the top layer of harvested crop within the clamp as evenly as possible prior to the compaction operation.

The open side of a silage clamp allows access for the working machine to distribute the crop. The harvested crop is located in the volume defined by the walls of the silage clamp.

To add harvested crop to the silage clamp, typically, a crop transportation vehicle, such as a trailer, transports a load of a harvested crop from a harvest location, e.g. a field, to the vicinity of the silage clamp, where it dumps the load. An operator of the working machine then moves portions of the dumped crop via the working arm and attachment to the silage clamp where the portions are deposited.

The quality of silage is dependent on the quality of the harvested crop that is used to produce the silage. For example, a lower quality harvested crop may contain unsuitable levels of contamination (from soil or manure, for example), moisture/dry matter, and/or sugar. When producing silage, a silage clamp may be filled with harvested crop harvested from different locations, at different times and/or during different weather conditions. As such, the quality of the harvested crop within the silage clamp, and thus the resulting silage, may vary considerably throughout the clamp.

Since it may be difficult to determine the quality of a portion of harvested crop being moved by the working machine by visual inspection alone, the operator may be unaware of the quality of the harvested crop they are depositing in the silage clamp. As such, the quality of the resulting silage and its variation throughout the clamp may be difficult to predict or determine.

The quality of silage can, for example, have a significant effect on cattle weight gain and milk production. As such, without information indicating silage quality and its variation in the clamp, agricultural output may be affected.

The present teachings seek to overcome or at least mitigate one or more problems associated with the prior art.

SUMMARY

According to a first aspect of the present teachings, there is provided a system for mapping one or more characteristics of a body of a harvested crop stored in a storage space, the system comprising:

- a controller;
- a first device assembly providing an input to the controller; and
- a second device assembly providing an input to the controller,
- wherein the controller is configured to determine one or more characteristics of each of a plurality of portions of the body of the harvested crop, such as dry matter content, moisture content, level of contamination, and/or one or more nutrient values, prior to the deposition of each of said portions in the storage space, based on at least the input from the first device assembly,
- wherein the controller is configured to determine a location at which each of said portions is deposited in the storage space based on at least the input from the second device assembly, and
- wherein the controller is configured to store the determined one or more characteristics and the determined location of each of said portions in a database.

Advantageously, storing the determined one or more characteristics and the corresponding determined locations of each of the portions of the body of the harvested crop in a database, may help a farmer or the like to determine how one or more characteristics of the body of harvested crop varies across the body. This could help said farmer to make more effective feed rationing plans for cattle subsequently being fed with the crop, for example during the winter.

Moreover, determining the one or more characteristics of each of the portions prior to their deposition in the storage space may simplify the process of determining the one or more characteristics relative to if they were determined after deposition of each portion in the storage space. Further, determining the one or more characteristics of each of the portions prior to their deposition in the storage space may enable each portion to be deposited in a desired location based on its determined one or more characteristics.

The system may be further configured to produce an output indicative of a location at which one or more of said portions is to be deposited in the storage space based on the determined one or more characteristics of said one or more portions.

Advantageously, by providing an output indicative of a location at which each of said portions is to be deposited in the storage space, the system may help to ensure that poorer quality harvested crop is located separately to higher quality harvested crop. For example, when the body of harvested crop is to be used to produce silage, the system may indicate that poorer quality harvested crop is to be placed at the edges of the body, where it tends to be harder to compact and more likely to be exposed to air, and may therefore result in a lower quality feed in any event, and higher quality harvested crop is to be placed in the center of the body, such that the quality of the resulting silage is improved.

The system may be further configured to produce an output indicating that a portion of a harvested crop is to be deposited separately from the storage space based on one or more characteristics of said portion determined by the controller based on at least the input from the first device assembly.

Advantageously, such an output may help to prevent a poor quality and/or a contaminated portion of harvested crop from being deposited on the body of the harvested crop, which may lead to contamination of the body and/or a reduction in quality of feed produced from the body, e.g. silage.

The second device assembly may be configured to determine the location at which each of said portions is deposited in the storage space in at least one of an x-direction, a y-direction, and/or a z-direction.

The second device assembly may include at least one of: a GNSS receiver, an inertial sensor, a tilt sensor, a steering angle sensor, and a travelling speed sensor, a LIDAR sensor, an electronic compass, and a camera.

Advantageously, these sensors are relatively low cost and simple to install, for example, on a working machine. The use of more than one of the sensors in combination may further improve the accuracy of the determination of the location at which each of the portions of the body of the harvested crop is deposited.

The input provided by the first device assembly to the controller may correspond to characteristics information originating from one or more sensors configured to sense the one or more characteristics of each of said portions.

Advantageously, such an input enables the determination of the one or more characteristics to be automated, which simplifies operation of the system.

The first device assembly may comprise a receiver device configured to receive the characteristics information via wireless communication.

Advantageously, the receiver device enables the system to receive the characteristics information automatically from one or more sensors remote from the system.

The determined one or characteristics of each of said portions may include a harvesting location of each of said portions.

The receiver device may be configured to receive the characteristics information via wireless communication with a harvested crop transport vehicle, such as a trailer or a forage wagon, a harvesting machine, such as a forage harvester, and/or a remote server.

Advantageously, such a configuration of the receiver device enables one or more sensors to obtain the characteristics information at a harvesting location during harvesting, e.g. by a forage harvester or a forage wagon, and then store the characteristics information on the harvested crop transportation vehicle, which may transport the harvested crop from the harvesting location to the storage space, or on a remote server. This enables the system to receive the characteristics information obtained at the harvesting location wirelessly and automatically, simplifying operation of the system.

The first device assembly may comprise a sensor assembly configured to sense one or more characteristics of each of said portions to determine the characteristics information.

Advantageously, the sensor assembly may enable the system to determine the characteristics information directly. This may enable the characteristics information to be determined immediately prior to a portion of the body of the harvested crop being deposited on the body, which may help to improve the accuracy of the mapping of the one or more characteristics of the body of harvested crop.

The sensor assembly may include at least one of: a nutrient sensor for sensing one or more nutrient values of a harvested crop, a moisture content sensor for sensing a moisture content of a harvested crop, a dry matter content sensor for sensing a dry matter content of a harvested crop, and/or a contamination sensor for sensing a level of contamination of a harvested crop.

The sensor assembly may include a near infrared sensor, and/or an image sensor.

According to a second aspect of the present teachings, there is provided a working machine comprising: the system according to the first aspect; a ground engaging structure for moving over the body of the harvested crop; and a load handling apparatus for handling a portion of a harvested crop and depositing said portion in the storage space.

Advantageously, the load handling apparatus may be used to progressively handle and deposit portions of a harvested crop on the body in order to enlarge the body.

The sensor assembly may include at least one sensor mounted to the load handling apparatus and configured to sense one or more characteristics of a portion of a harvested crop being handled by the load handling apparatus.

Advantageously, mounting at least one sensor on the load handling apparatus enables one or more characteristics of a portion of harvested crop to be determined automatically whilst said portion is being moved towards or over the body for deposition.

The load handling apparatus may comprise a working arm and an attachment mounted to a distal end of the working arm, the attachment comprising a load handling implement, such as a fork, configured to handle a portion of a harvested crop. The sensor assembly may comprise at least one sensor mounted to the load handling implement.

Advantageously, mounting at least one sensor to the load handling implement may enable the at least one sensor to be in contact with or adjacent to a portion of harvested crop when sensing the one or more characteristics of said portion, which may improve the accuracy of such sensing.

The working machine may further comprise a weight sensor configured to determine a weight of a portion of a harvested crop being handled by the load handling apparatus, the weight sensor providing an input to the controller, and/or further comprise a volume sensor configured to determine a volume of a portion of a harvested crop being handled by the load handling apparatus, the volume sensor providing an input to the controller.

The volume sensor may comprise an image sensor and/or a lidar device.

Advantageously, the weight/volume sensor may enable the size of each portion of the body of harvested crop to be determined. This may help to indicate a granularity of the mapping of the one or more characteristics of the body of the harvested crop.

According to a third aspect of the present teachings, there is provided an attachment for mounting to a working arm of a working machine, the attachment comprising: a load handling implement, such as a fork, configured to handle a portion of a loose harvested crop; and at least one sensor mounted to the load handling implement, wherein the at least one sensor is configured to determine one or more characteristics of a portion of a harvested crop being handled by the load handling implement, such as dry matter content, moisture content, level of contamination and/or one or more nutrient values.

The at least one sensor may include at least one of: a nutrient sensor for sensing one or more nutrient values of a harvested crop, a moisture content sensor for sensing a moisture content of a harvested crop, a dry matter content sensor for sensing a dry matter content of a harvested crop, and/or a contamination sensor for sensing a level of contamination of a harvested crop.

The at least one sensor may include a near infrared sensor, and/or an image sensor.

The load handling implement may be a fork comprising a back support and a plurality of tines extending from said back support. The at least one sensor may be mounted to said back support and/or at least one of said tines.

The load handling implement may be a silage fork or a buckrake.

The at least one sensor may include a sensor mounted to one of the tines. Said sensor may be mounted to a portion of said tine closer to the back support relative to a free end of said tine.

According to a fourth aspect of the present teachings, there is provided a computer implemented method for mapping one or more characteristics of a body of a harvested crop stored in a storage space, the method comprising:

(a) determining, via a first device assembly, one or more characteristics of each of a plurality of portions of the body of the harvested crop, such as dry matter content, moisture content, level of contamination, and/or one or more nutrient values, prior to the deposition of each of said portions in the storage space;

(b) determining, via a second device assembly, a location at which each of said portions is deposited in the storage space; and (c) storing, in a database, the determined one or more characteristics and the determined location of each of said portions.

The method may further comprise: producing an output indicative of a location at which one or more of said portions is to be deposited in the storage space based on the determined one or more characteristics of said one or more portions.

The method may further comprise: producing an output indicating that a portion of a harvested crop is to be deposited separately from the storage space based on one or more characteristics of said portion determined via the first device assembly.

In step (a) of the method, the one or more characteristics of each of said portions may be determined, via the first device assembly, from characteristics information originating from one or more sensors configured to sense the one or more characteristics of each of said portions.

The first device assembly may comprise a receiver device. Step (a) may further comprise: the receiver device receiving the characteristics information via wireless communication.

The determined one or characteristics of each of said portions may include a harvesting location of each of said portions.

The receiver device may receive the characteristics information via wireless communication with a harvested crop transport vehicle, such as a trailer or a forage wagon, a harvesting machine, such as a forage harvester, and/or a remote server.

The first device assembly may comprise a sensor assembly. Step (a) may further comprise: sensing, via the sensor assembly, one or more characteristics of each of said portions to determine the characteristics information.

The sensor assembly may include at least one of: a nutrient sensor for sensing one or more nutrient values of a harvested crop, a moisture content sensor for sensing a moisture content of a harvested crop, a dry matter content sensor for sensing a dry matter content of a harvested crop, and/or a contamination sensor for sensing a level of contamination of a harvested crop.

The sensor assembly may include a near infrared sensor, and/or an image sensor.

The method may be performed by a working machine comprising: the first device assembly; the second device assembly; a ground engaging structure for moving over the body of the harvested crop; and a load handling apparatus for handling a portion of a harvested crop and depositing said portion in the storage space.

The working machine may comprise a weight sensor. The method may further comprise: determining, via the weight sensor, a weight of a portion of a harvested crop being handled by the load handling apparatus.

The working machine may comprise a volume sensor. The method may further comprise: determining, via the volume sensor, a volume of a portion of a harvested crop being handled by the load handling apparatus.

The volume sensor may comprise an image sensor and/or a lidar device.

BRIEF DESCRIPTION OF THE DRAWINGS

Embodiments are now disclosed by way of example only with reference to the drawings, in which.

DESCRIPTION

Figure 1:
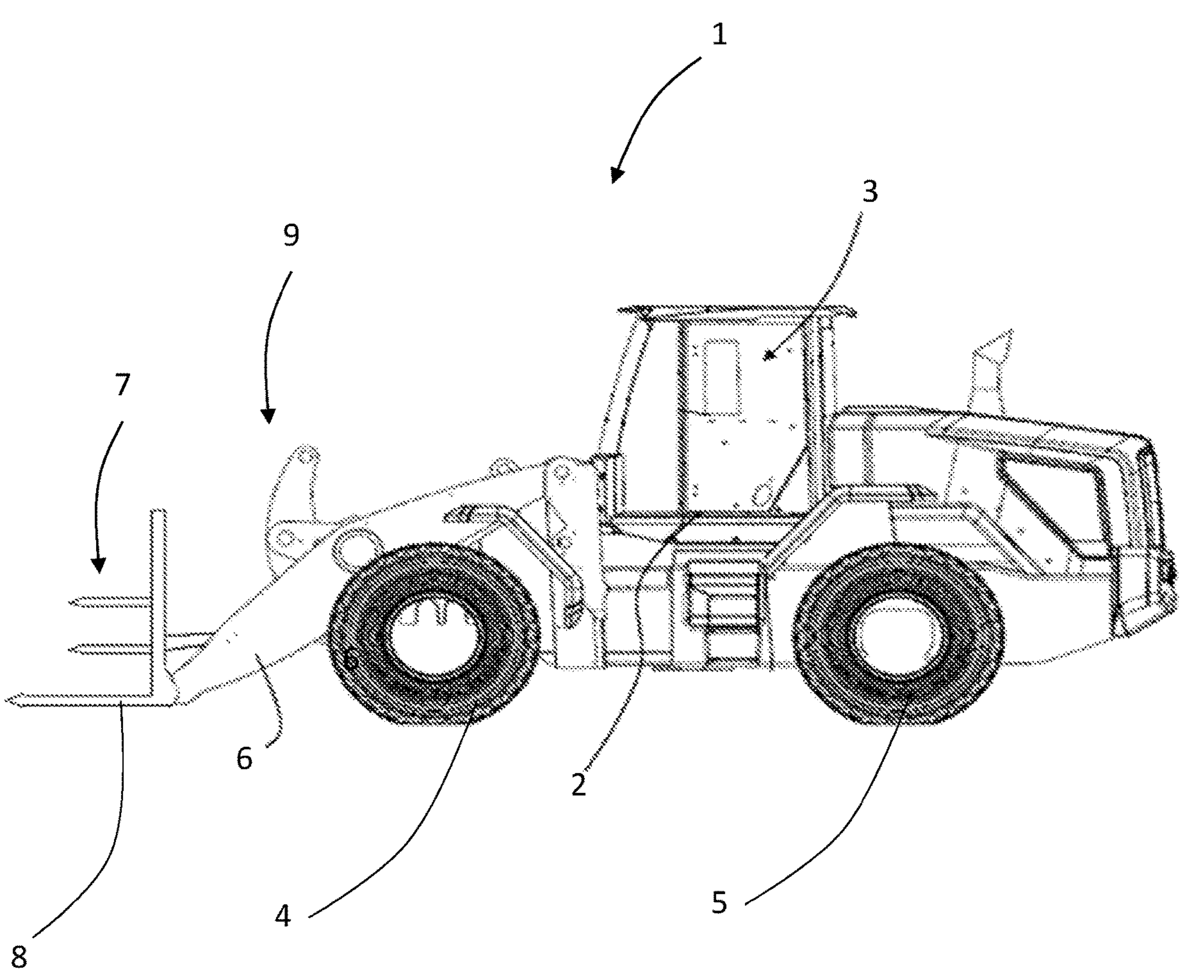
FIG. 1 is a side view of a working machine of an embodiment of the present teachings.

Referring firstly to FIG. 1, an embodiment includes a working machine 1 which may be a material handling machine. In this embodiment, the material handling machine 1 is a wheeled loading shovel. In alternative embodiments, the working machine 1 may be a telescopic handler or a tractor, for example.

The machine 1 includes a machine body 2. The body 2 may include an operator structure 3 to accommodate a machine operator, for example, an enclosed operator structure from which an operator can operate the machine 1. In other embodiments, the working machine 1 may have an open canopy structure (not shown) for the operator.

The machine 1 has a ground engaging propulsion structure 4, 5 comprising a first axle and a second axle, each axle being coupled to a pair of wheels (two wheels 4, 5 are shown in FIG. 1 with one wheel 4 connected to the first axle and one wheel 5 connected to the second axle). The first axle may be a front axle and the second axle may be a rear axle. One or both of the axles may be coupled to a motor or engine which is configured to drive movement of one or both pairs of wheels 4, 5. Thus, the wheels 4, 5 may contact a ground surface and rotation of the wheels 4, 5 may cause movement of the working machine 1 with respect to the ground surface.

In other embodiments, the ground engaging propulsion structure may comprise tracks or rollers. In other embodiments, the drive transmission may not be operated by the motor via a direct mechanical linkage, but instead the motor may drive a hydraulic pump, which subsequently provides traction via one or more hydraulic motors that are drivingly connected to the wheels or tracks. Alternatively, the drive transmission may comprise an electric motor for providing traction to the wheels or tracks.

A load handling apparatus 9 is coupled to the machine body 2. The load handling apparatus 9 includes a working arm 6 mounted to the front of the machine body 2. The load handling apparatus 9 includes an attachment 7 mounted to a distal end of the working arm 6. The attachment 7 includes a load handling implement 8, in this case a fork, configured to handle a portion of a loose harvested crop. In alternative embodiments, the load handling implement may be any suitable implement, such as a grab or buckrake. The working arm 6 raises and lowers the load handling implement 8.

By 'portion of a loose harvested crop', it is intended to mean a portion of a harvested crop in which the individual components of the crop (e.g. blades of grass) are free to move relative to each other; for example, a portion of a harvested crop that has not been bound, bailed, compacted or wrapped.

The working machine 1 also include a hydraulic fluid circuit arranged to provide hydraulic fluid to one or more hydraulic actuators for performing working operations such as moving the working arm 6 and the load handling implement 8 of the working machine 1.

Figure 2A:
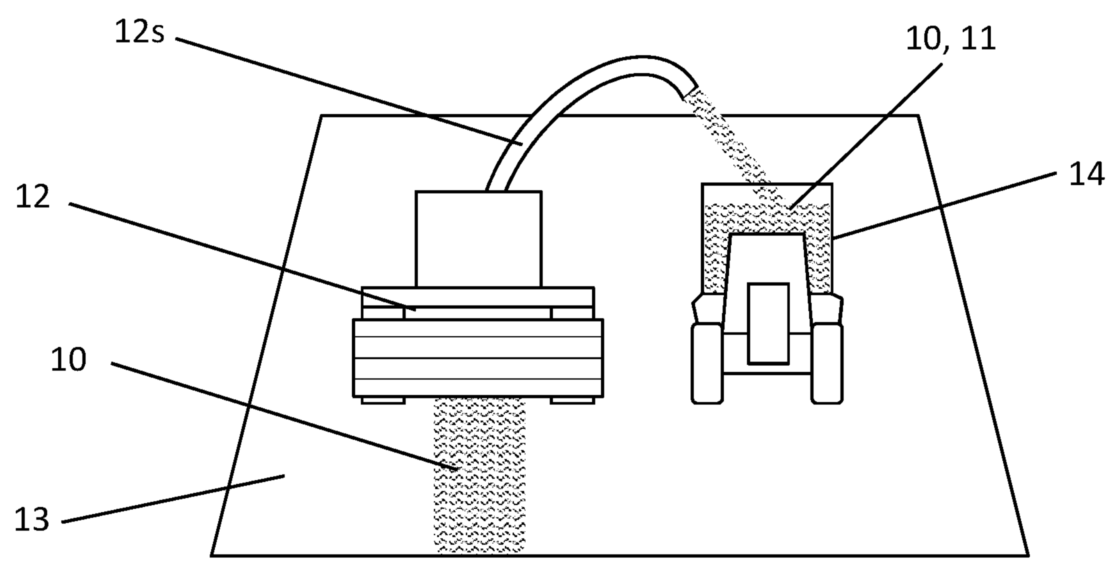
FIGS. 2A-2C are schematic representations of steps of a silage making process.
Figure 2B:
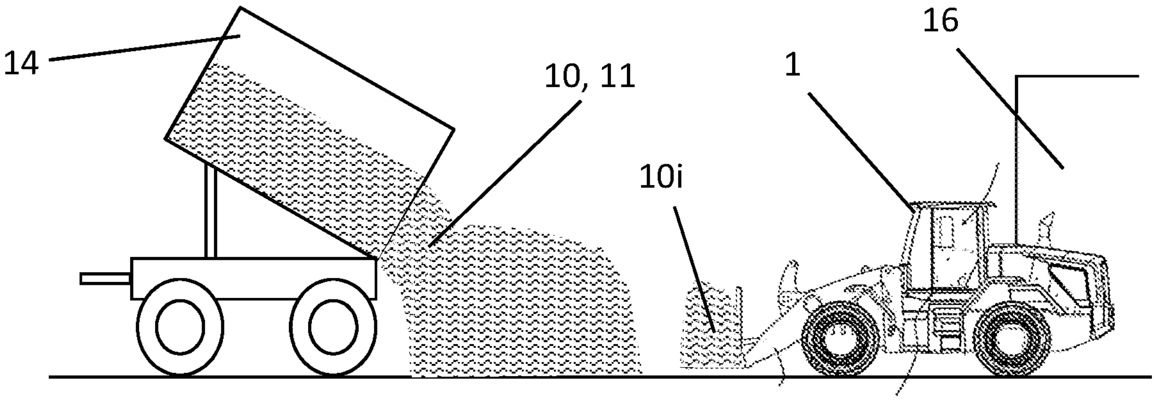
Figure 2C:
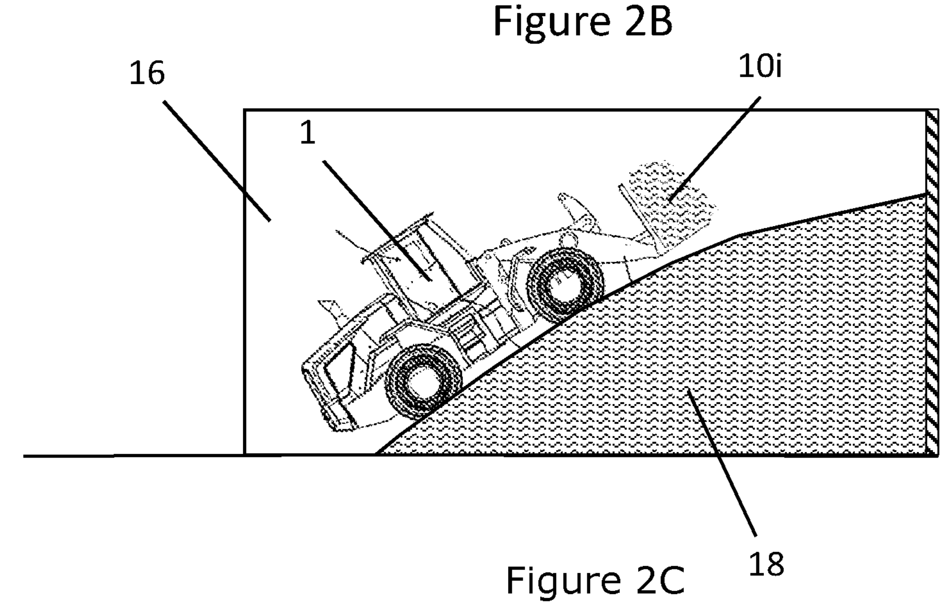

As illustrated in FIGS. 2A-C, the working machine 1 may be used to handle portions of a harvested crop and to deposit said portions in a storage space as part of a silage making process.

With reference to FIG. 2A, in a first stage of the silage making process, a crop 10, such as grass, is harvested by a harvesting machine 12, such as a forage harvester, in a harvesting location 13, such as a field. In FIG. 2A, the harvesting machine 12 transfers a load 11 of the harvested crop 10 to a harvested crop transport vehicle 14, such as a trailer. In FIG. 2A, the load 11 is blown in the transport vehicle via a spout 12*s* of the harvesting machine 12.

With reference to FIG. 2B, in a second stage of the silage making process, the transport vehicle 14 transports the load 11 of the harvested crop 10 from the harvesting location 13 to the vicinity of a storage space 16, at which location the transport vehicle 14 dumps the load 11 of the harvested crop 10. The storage space 16 may be a pit or a clamp. The working machine 1 handles portions 10*i* of the dumped load 11 of the harvested crop 10 via the load handling implement 8 and moves each portion 10*i* to the storage space 16.

In alternative embodiments (not shown), the harvesting machine may additionally or alternatively transport the harvested crop 10 from the harvesting location 13 to the vicinity of the storage space 16; i.e. the harvesting machine and the harvested crop transport vehicle may be the same vehicle. For example, the harvesting machine/harvested crop transport vehicle may be a forage wagon.

With reference to FIG. 2C, in a third stage of the silage making process, the working machine 1 deposits each portion 10*i* in the storage space 16 to form a body of a harvested crop 18, which is stored in the storage space 16. The ground engaging propulsion structure 4, 5 of the working machine 1 is suitable for moving over the body 18 to enable the working machine 1 to deposit portions 10*i* on top of the body 18.

Although not illustrated, once the body 18 has reached a desired volume, the working machine 1 may compact the body 18 before the body 18 is covered in an impermeable sheet to enable silage to be produced via fermentation of the body 18.

Figure 3:
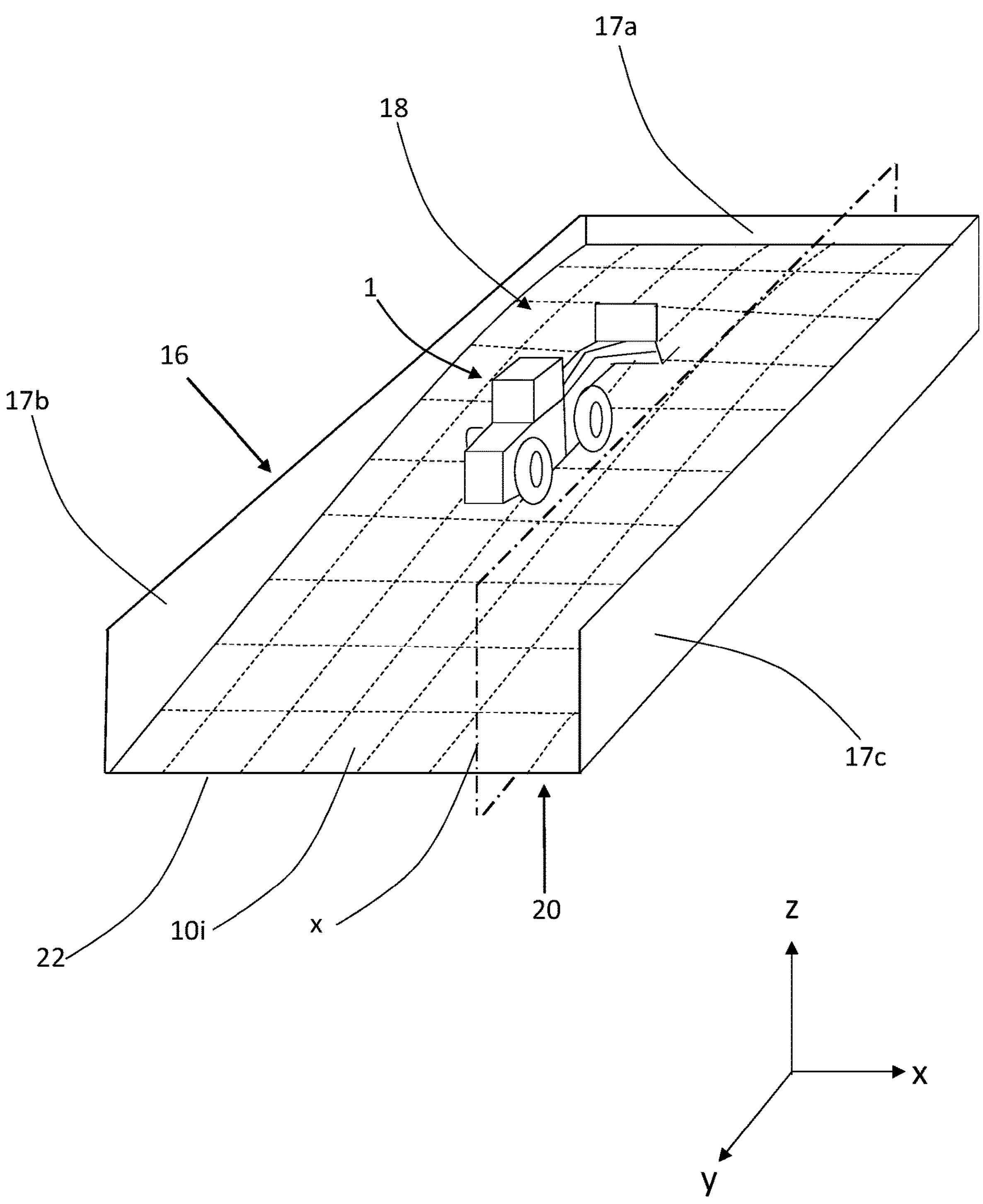
FIG. 3 is an isometric view of the working machine of FIG. 1 depositing a portion of a harvested crop on a body of a harvested crop.

In this embodiment, as illustrated in FIG. 3, the storage space 16 is generally rectangular. The storage space 16 includes three walls 17*a-c* and a floor 20, which define an internal volume for containing the body of the harvested crop 18. The storage space 16 includes an opening 22 at one side to allow for the working machine 1 to enter the storage space 16 and access the body of the harvested crop 18. It shall be appreciated that any suitable storage space may be used, for example a non-rectangular storage space, or the walls 17*a-c* may be omitted and the crop stored in a mound deposited on a surface.

Figure 4:
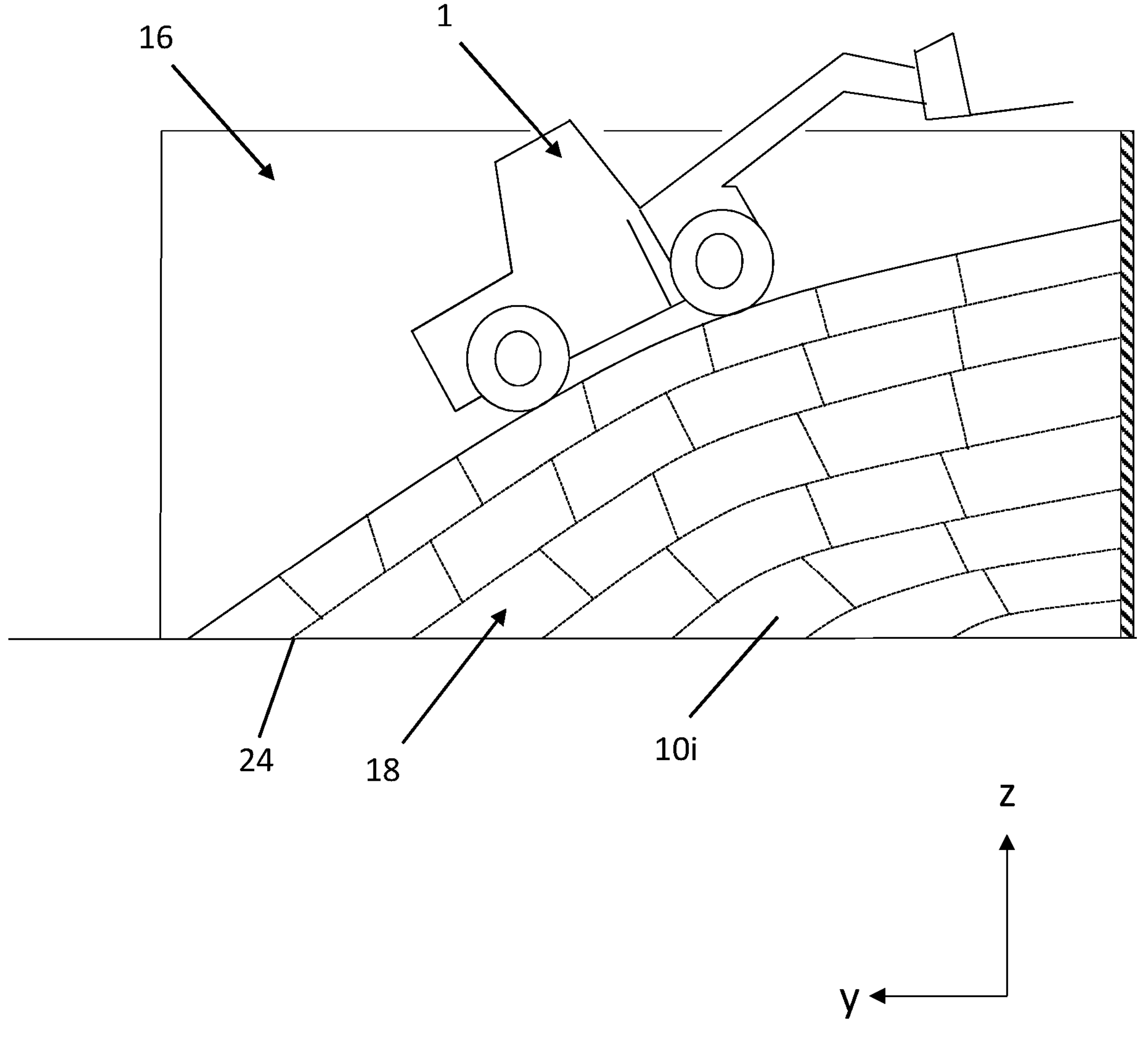
FIG. 4 is a sectional view through the plane x of FIG. 3.

FIG. 4 is a section view of the body of harvested crop 18 through the plane x of FIG. 3. FIG. 4 illustrates that the harvested crop 10 is deposited in layers 24, each layer 24 formed from one or more portions 10*i*.

Note that in FIGS. 3 and 4, the portions 10*i* are represented as substantially cuboidal blocks of harvested crop 10 for reasons of clarity. It will be appreciated that in reality, the portions 10*i* may have complex and non-uniform shapes.

The working machine 1 will compact the body of the harvested crop 18, via the ground engaging propulsion structure 4, 5, by passing over the body 18 whilst the implement 8 distributes an additional top layer of harvested crop 10 onto the body 18. Periodically the working machine 1 will typically perform a pure compacting operation where it solely passes over the body of harvested crop 18 in a more methodical fashion. This process is repeated such that the implement 8 progressively deposits more harvested crop 10 onto the body of the harvested crop 18 as it is harvested in order to enlarge the body 18 between compaction operations.

Typically, in the prior art, portions of a harvested crop 10*i* are deposited in a storage space by a working machine with little or no consideration of the quality of the portions of the harvested crop 10*i* being deposited. As such, the quality of the resulting silage and its variation within the storage space may be difficult to predict or determine. In addition a contaminated portion of harvested crop may which is deposited amongst uncontaminated harvested crop may leach into and may harm the quality of silage made from the surrounding uncontaminated crop. The present teachings seek to solve or at least mitigate these problems.

Figure 5:
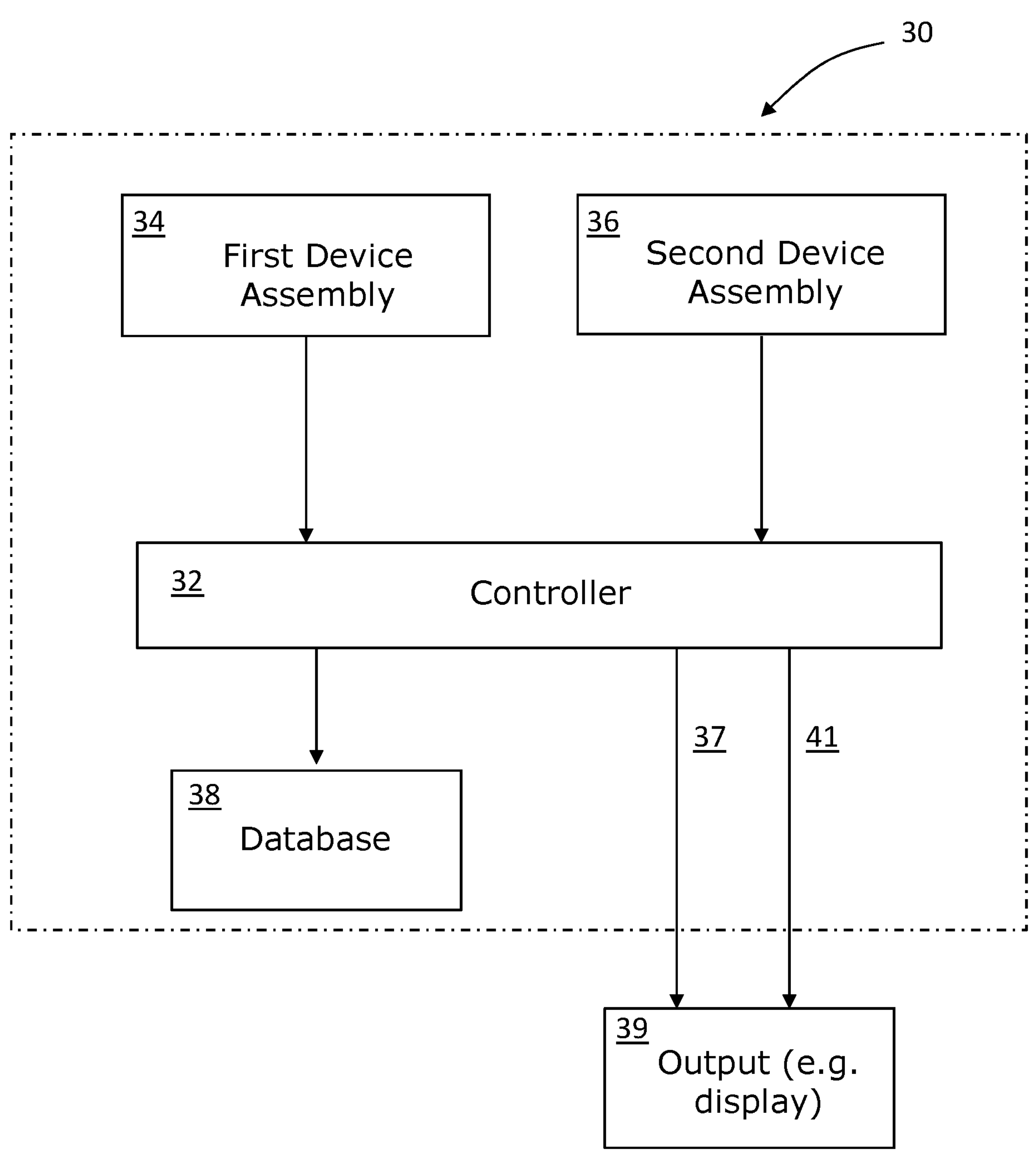
FIG. 5 is a block diagram of a system for mapping one or more characteristics of the body of the harvested crop according to an embodiment of the present teachings.

With reference to FIG. 5, the working machine 1 includes a system 30 for mapping one or more characteristics of the body of the harvested crop 18 stored in the storage space 16. Examples of such characteristics include dry matter content/moisture content, level of contamination, and/or one or more nutrient values. Mapping one of more characteristics of the body of the harvested crop 18 may enable a farmer or the like to predict or determine the quality of silage produced from the body 18 and its variation within the storage space 16. This may then enable them to pre-emptively plan to mix silage from different locations in the body of the harvested crop 18 to achieve suitable quality and/or augment the silage with additional feedstuffs to achieve a suitable level of overall feed quality.

The system 30 includes a controller 32 (e.g. a suitable microprocessor controller), a first device assembly 34 providing an input to the controller 32, and a second device assembly 36 providing an input to the controller 32. The controller 32 is configured to determine one or more characteristics of each of the plurality of portions 10*i* of the body of the harvested crop 18 based on at least the input from the first device assembly 34. Moreover, the controller 32 is configured to determine a location at which each of the plurality of portions 10*i* of the body of the harvested crop 18 is deposited in the storage space 16 based on at least the input from the second device assembly 36. Furthermore, the controller 32 is configured to store the determined one or more characteristics of each of said portions 10*i* and the determined location at which each of said portions 10*i* is deposited in the storage space 16 in a database 38.

The controller 32 is configured to determine the one or more characteristics of each of the portions 10*i* prior to the deposition of each of the portions 10*i* in the storage space 16. Advantageously, determining the one or more characteristics of each of the portions 10*i* prior to their deposition in the storage space 16 enables each portion 10*i* to be deposited in a desired location based on its one or more determined characteristics.

The input provided by the first device assembly 34 to the controller 32 corresponds to characteristics information originating from one or more sensors configured to sense the one or more characteristics of each of the portions 10*i*. In embodiments described in more detail below the one or more sensors may be mounted to the harvesting machine 12, to the transport vehicle 14, and/or to the working machine 1.

In the present embodiment, the first device assembly 34 includes a sensor assembly 35 configured to sense one or more characteristics of each of the portions 10*i*. The sensor assembly 35 includes at least one of: a nutrient sensor for sensing one or more nutrient values (e.g. protein, fat, fiber, sugar and the like) of a portion 10*i*, a moisture content sensor for sensing the moisture content of a portion 10*i*, a dry matter content sensor for sensing the dry matter content of a portion 10*i*, and/or a contamination sensor for sensing a level of contamination of a portion 10*i*.

The sensor assembly 35 may include a near infrared (NIR) sensor configured to sense, for example, the moisture content and/or one or more nutrient values of a portion 10*i*. An example of such a NIR sensor is the EvoNIR 4.0 Analyzer provided by Dinamica Generale S.p.A of Poggio Rusco, Mantua, Italy. It will be appreciated that the dry matter content of a portion 10*i* may be determined from the sensed moisture content of said portion 10*i*.

Additionally or alternatively, the sensor assembly 35 may include an image sensor configured to capture one or more images of a portion 10*i*. Said image sensor or the controller 32 may compare the one or images captured by the image sensor to reference images of the harvested crop 10 forming the portion 10*i* in order to determine a level of contamination of said portion 10*i*.

Additionally or alternatively, the sensor assembly 35 may include a moisture sensor, such as a moisture probe, configured to sense the moisture content of a portion 10*i*.

The sensor assembly 35 includes at least one sensor mounted to the load handling apparatus 9 of the working machine 1, which is configured to sense one or more characteristics of a portion of a harvested crop 10*i* being handled by the load handling apparatus 9.

Figure 6:
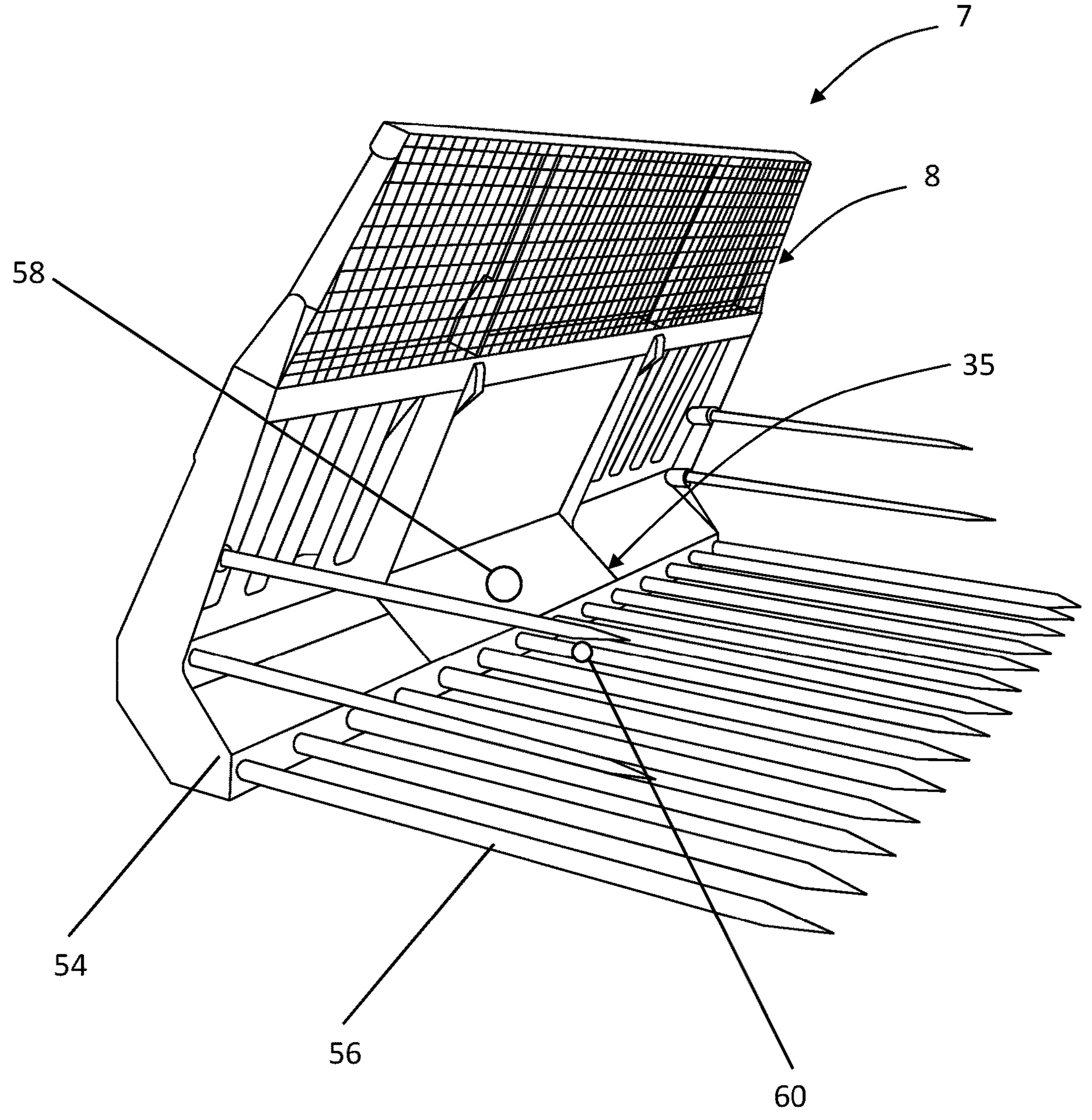
FIG. 6 is a perspective view of an attachment of the working machine of FIG. 1.

With reference to FIG. 6, the sensor assembly 35 includes at least one sensor mounted to the load handling implement 8. FIG. 6 shows a perspective view of the attachment 7 of the working machine 1 according to the present embodiment, in which the load handling implement 8 is a fork, and in particular a silage fork. The fork 8 includes a back support 54 and a plurality of tines 56 extending from the back support 54. The spacing between the tines 56 is such that the fork 8 can handle a portion of a loose harvested crop without losing a significant amount of the crop through the gaps between the tines 56.

The sensor assembly 35 includes at least one sensor 58 mounted to the back support 54, and/or at least one sensor 60 mounted to at least one of the tines 56. The sensors 58, 60 are represented schematically by circles in FIG. 6.

The at least one sensor 58 may be mounted in a substantially central position on the back support 54, as shown in FIG. 6, to increase the likelihood that the at least one sensor 58 will be adjacent a portion 10*i* being handled by the fork 8 to enable sensing of said portion 10*i*. For example, the at least one sensor 58 may be located at or towards a transverse mid-point of the back support 54. Moreover, the at least one sensor 58 may be located at or towards the bottom of a face of the back support 54 from which the tines 56 extend, just above the tines.

The at least one sensor 60 may include a sensor 60 mounted to a portion of one of the tines 56 that is closer to the back support 54 relative to a free end of said tine 56. The free ends of the tines 56 may be pointed as shown in FIG. 6. Advantageously, mounting the sensor 60 to the tine 56 such that it is closer to the back support 54 relative to the free end of the tine 56 may increase the likelihood that the sensor 60 will be adjacent a portion 10*i* being handled by the fork 8 to enable sensing of said portion 10*i*. The at least one sensor 60 may be mounted within at least one of the tines 56 in order to protect the at least one sensor 60 from damage caused by contact with a portion 10*i* being handled by the fork 8. Moreover, the at least one sensor 60 may be located in at least one of the tines 56 at or towards a transverse mid-point of the back support 54.

For example, a NIR sensor, a moisture sensor and/or an image sensor may be mounted within at least one the tines 56. Each sensor may be configured to determine one or more characteristics of a portion 10*i* adjacent to the at least one tine 56 when the fork 8 handles said portion 10*i*.

Advantageously, mounting one or more sensors to the load handling implement 8 enables one or more characteristics of a portion 10*i* being handled by the load handling implement 8 to be sensed immediately prior to said portion 10*i* being deposited in the storage space 16. This may help to increase the accuracy of the one or more characteristics determined for each portion 10*i*.

In alternative embodiments (not shown), the load handling implement may be in the form of a dozer blade, and the sensor assembly 35 may include at least one sensor mounted to the dozer blade. Alternatively, the load handling implement may be in the form of a silage spreader including a rotatable drum and a plurality of blades extending radially from said drum, and the sensor assembly 35 may include at least one sensor mounted to the silage spreader (e.g. to at least one of the blades).

The sensor assembly 35 may include a weight sensor configured to determine a weight of a portion of a harvested crop 10*i* being handled by the load handling apparatus 9, the weighing sensor providing an input to the controller 32. The weight sensor may be any suitable sensor, such as a load cell mounted to the load handling apparatus 9, for example, or a sensor mounted to the working machine 1 that can infer the weight e.g. from hydraulic cylinder pressures or rear axle sensors in conjunction with information relating to the mass of the load handling apparatus 9 and its position relative to the working machine 1. An example of such a system is the Loadmaster a100 provided by RDS Technology Limited of Stroud, Gloucestershire, United Kingdom. The controller 32 may store the determined weight of each of the portions 10*i* of the body 18 as a characteristic of each of said portions 10*i* in the database 38.

Additionally or alternatively, the sensor assembly 35 may include a volume sensor configured to determine a volume of a portion of a harvested crop 10*i* being handled by the load handling apparatus 9, the volume sensor providing an input to the controller 32. The volume sensor may be any suitable sensor, and may include an image sensor and/or a lidar device mounted to the load handling apparatus 9, for example. The controller 32 may store the determined volume of each of the portions 10*i* of the body 18 as a characteristic of each of said portions 10*i* in the database 38.

Advantageously, storing the weight and/or volume of each portion 10*i* of the body 18 in the database 38 provides an indication of the size of each portion 10*i*, and thus the size of the body 18.

With reference to FIG. 5, the system 30 is configured to produce an output 37 indicative of a location at which one or more of the portions 10*i* is to be deposited in the storage space 16 based on the determined one or more characteristics of said one or more portions 10*i*. The system 30 provides the output 37 to an output device 39, such as a display, for displaying a visual indicator of the output 37. The output device 39 may be located in the operator structure 3 of the working machine 1, for example. The visual indicator of the output 37 may correspond to a marker on a map of the storage space 16 indicating a location at which a portion 10*i* is to be deposited by the working machine 1.

As shown in FIG. 5, the system 30 is configured to produce an output 41 indicating that a portion of the load 11 is to be deposited separately from the storage space 16 based on one or more characteristics of said portion determined by the controller 32 based on at least the input from the first device assembly 34. The system 30 provides the output 41 to the output device 39. The output device 39 displays a visual indicator of the output 41, such as a written message stating that the portion 10*i* is not to be deposited in the storage space 16, for example.

It shall be appreciated that in alternative embodiments, the output device may be any suitable visual indicator, for example a light. Alternatively, the output device may be any suitable device, such as an audio indicator.

With reference to FIGS. 3 to 5, the second device assembly 36 is configured to determine the location at which each of the portions 10*i* is deposited in the storage space 16 in at least one of an x-direction, a y-direction, and/or a z-direction. As shown in FIGS. 3 and 4, the x, y and z directions are mutually orthogonal and enable a location at which each of the portions 10*i* is deposited in the storage space 16 to be specified using a Cartesian coordinate system.

In the present embodiment, the second device assembly 36 includes a global navigation satellite system (GNSS) receiver for detecting the absolute position of the working machine 1. The GNSS receiver may be located at any suitable location on the working machine 1, for example in the operator cab 3. The GNSS receiver may be a GNSS real-time kinetic positioning (RTK) receiver, or any other known system of obtaining increased accuracy from a standard GNSS system. GNSS RTK receivers improve the accuracy of the position detection by using a local station, for example a station within 15 km, to calibrate the absolute position from a GNSS satellite with the position outputted by the receiver. As such accuracy may be within millimeters in the x and y directions and centimeters or at least tens of centimeters in the z direction.

GNSS RTK receivers have accuracy benefits compared to traditional systems such as standard GPS systems, and compared to more simplistic sensors such as inertial sensors, as well as being relatively low cost. This particularly beneficial when determining the position of the working machine 1 in the z-direction, because the error associated with alternative sensors and GNSS systems is relatively high compared to the z-displacement of the working machine 1. It shall be appreciated that in alternative embodiments, any suitable GNSS system with a suitable level of accuracy may be used.

To determine the location at which a portion 10*i* is deposited in the storage space 16, the controller 32 receives the absolute position of the working machine 1 from the GNSS receiver when the controller 32 determines that the portion 10*i* is deposited. If the GNSS receiver is spaced from the load handling implement 8, the controller 32 may correct the location determined by the GNSS receiver to account for the distances in the x, y and/or z directions between the GNSS receiver and the load handling implement 8.

The controller 32 may determine when a portion 10*i* is deposited in the storage space 16 via any suitable means. For example, the controller 32 may determine when a portion 10*i* is deposited in the storage space 16 based on the input(s) received from the weight sensor and/or volume sensor of the sensor assembly 35. Additionally or alternatively, the system 30 may include a camera providing an input to the controller 32, the camera arranged such that the field of view of the camera includes the load handling implement 8. The controller 32 may determine when a portion 10*i* is deposited in the storage space 16 based on the input received from said camera.

In addition to or instead of a GNSS receiver, the second device assembly 36 may include an inertial sensor for detecting the position of the working machine 1 relative to the body of the harvested crop 18. The inertial sensor may detect the relative position of the working machine 1 relative to the body of harvested crop 18 in the x-direction and the y-direction. The inertial sensor may use an accelerometer to detect the linear acceleration of the working machine 1, and a gyroscope to detect the rotational rate of the working machine 1. The inertial sensor may be located at any suitable location on the working machine 1 for example on the underside of the machine body 2. Such sensors are generally low cost, compact and robust, being found in numerous electronic devices such as smartphones.

Additionally or alternatively, the second device assembly 36 may include a tilt sensor for measuring the angle of the working machine 1 relative to a fixed axis. Tilt sensors are commonly fitted to working machines, and can be utilized by the controller 32 to determine when the angle of the working machine 1 exceeds a predetermined tilt angle relative to the fixed axis. This can be indicative that the working machine 1 has mounted the body of the harvested crop 18. If an initial height of the body of harvested crop 18 is inputted into the controller 32, the controller 32 can use the height to determine an inclination threshold indicative that the working machine 1 has mounted the body 18, as opposed to that the working machine 1 is travelling on an uphill gradient. Additionally, the tilt sensor may be used to determine the z-displacement of the working machine 1 by storing the input from the tilt sensor indicative of the angle of the ground over which the working machine 1 is moving. The tilt sensor may be used in combination with any of the above sensors to detect the z-displacement of the working machine 1.

Additionally or alternatively, the second device assembly 36 may include a working machine travelling speed sensor and a steering angle sensor for detecting the position of the working machine 1 relative to the body of the harvested crop 18. The input from the travelling speed sensor can be used by the controller 32 to determine the displacement of the working machine 1 from a datum position, for example the opening 22 of the storage space 16. The input from the steering angle sensor can be used by the controller 32 to determine the angle at which the working machine 1 has travelled relative to a fixed axis, for example the y-axis. The relative position of the working machine 1 in polar coordinates is therefore determined from the sensor inputs.

Additionally or alternatively, the second device assembly 36 may include a machine vision system such as a light detection and ranging (LIDAR) sensor system to determine the relative position of the working machine 1. The LIDAR system uses the reflection of lasers or light beams off the walls 17*a*, 17*b*, 17*c* of the storage space 16 to determine the position of the working machine 1.

Additionally or alternatively, said machine vision system may be configured to determine the location at which a portion 10*i* is deposited in the storage space 16 by tracking the portion 10*i* as it leaves the load handling implement 8 and is deposited in the storage space 16. For example, the machine vision system may include a LIDAR sensor system and/or a camera system.

Additionally or alternatively, the second device assembly 36 may include an electronic compass to determine the position of the working machine 1 i.e. to provide an orientation of the machine 1 relative to the body of the harvested crop 18. This is beneficial to enhance the information provided by the GNSS system.

In some instances, the working machine 1 may move with respect to the storage space 16 whilst depositing a portion 10*i* in the storage space 16, causing the portion 10*i* to be spread along the x and/or y directions of the storage space 16. In such instances, the controller 32 may track the spread of the portion 10*i* based on the inputs received from the second device assembly 36 and one or both of the weight sensor and the volume sensor of the sensor assembly 35. For example, based on the reduction in sensed weight/volume of the portion 10*i* handled by the load handling implement 8 and the location of the working machine 1 determined by the second device assembly 36, the controller 32 may determine an area in the storage space 16 over which the portion 10*i* is spread. Moreover, the controller 32 may determine the distribution of weight and/or volume of the portion 10*i* over the determined area. The controller 32 may determine the location at which the portion 10*i* is deposited in the storage space 16 as the centroid of the determined area. Alternatively, the controller 32 may determine a plurality of locations at which the portion 10*i* is deposited in the storage space 16 based on the determined area.

Figure 7:
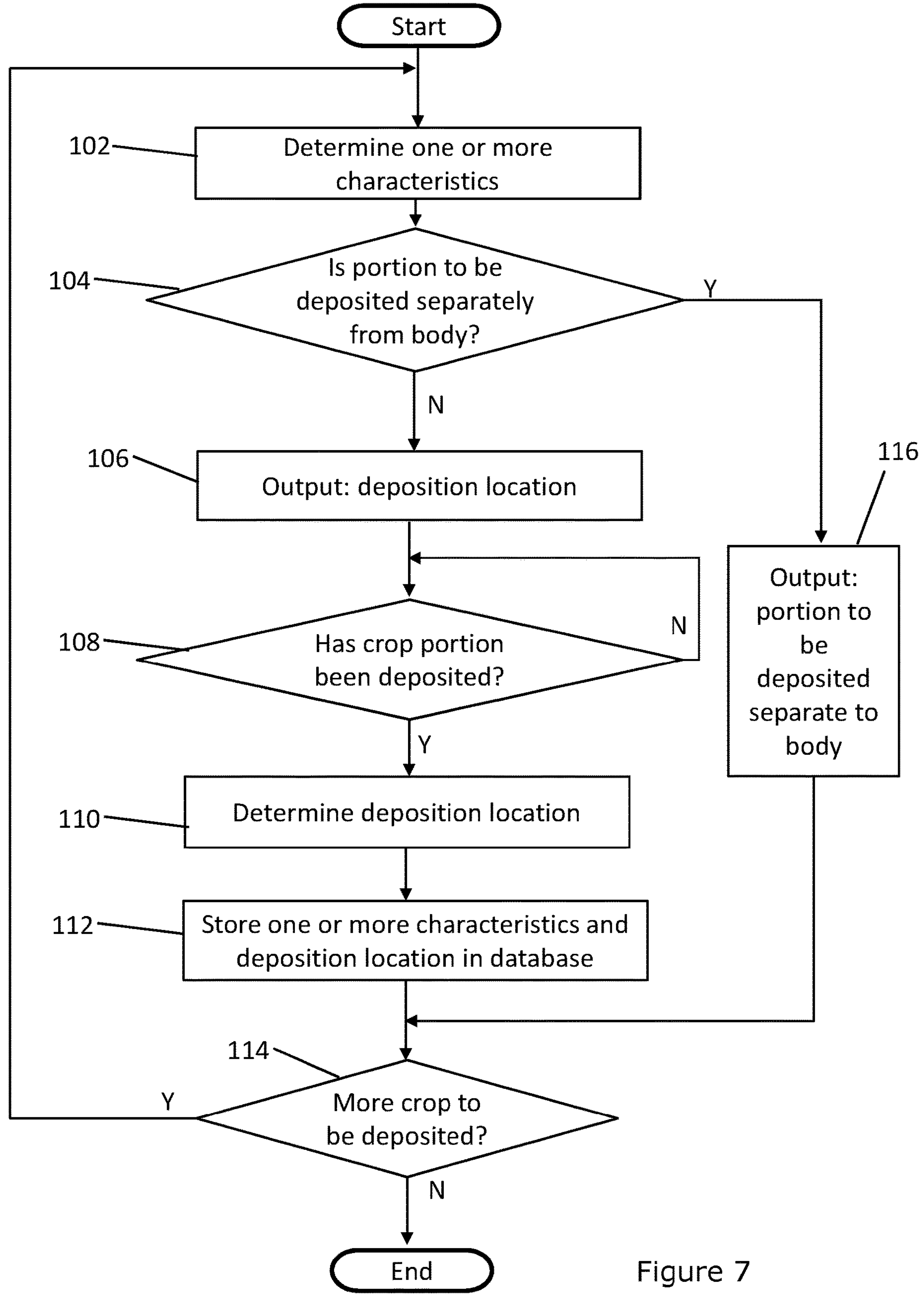
FIG. 7 is a flow chart of the system of FIG. 5.

FIG. 7 illustrates an embodiment of a computer implemented method followed by the system 30 for mapping one or more characteristics of the body of the harvested crop 18 stored in the storage space 16.

Prior to carrying out the method described below, certain parameters need to be obtained or input into the system. These parameters may include the location and dimensions of the storage space 16. These parameters may also include those of the working machine 1/load handling implement 8, such as an offset between the GNSS sensor and the load handling implement 8, which enables the location that a portion 10*i* is deposited to be accurately determined.

In step 102, the load handling implement 8 of the working machine 1 picks up a portion 10*i* of the load of the harvested crop 11 which has been dumped by the transport vehicle 14 in the vicinity of the storage space 16, as illustrated in FIG. 2B. The controller 32 then determines the one or more characteristics of the portion 10*i* being handled by the load handling implement 8 based on the input received from the sensor assembly 35 of the first device assembly 34.

In step 104, the controller 32 determines whether, based on the one or more determined characteristics of the portion 10*i*, the portion 10*i* is to be deposited separately from the storage space 16.

The controller 32 may determine from one or more characteristics of the portion 10*i* of the load 11 being handled by the working machine 1 that said portion 10*i* includes an unsuitable level of contamination. Therefore, to prevent said portion 10*i* from contaminating the body 18, the output 41 may indicate that said portion 10*i* is to be deposited separately from the storage space 16 and thus the body 18.

If the controller 32 determines that the portion 10*i* is to be deposited separately from the storage space ('Y'), the method proceeds to step 116. If the controller 32 determines that the portion 10*i* is not to be deposited separately from the storage space ('N'), i.e. the portion 10*i* is to be deposited in the storage space 16, the method proceeds to step 106.

In step 116, the system 30 produces the output 41 indicating that the portion 10*i* is to be deposited separately from the storage space 16. The output 41 may be provided to an operator of the working machine 1 via the output device 39 as previously described, who may then proceed to deposit the portion 10*i* in a location separate from the storage space 16. The method then proceeds to step 114, described below.

In step 106, the controller 32 determines a location at which the portion 10*i* is to be deposited in the storage space 16 based on the determined one or more characteristics of the portion 10*i*.

When producing silage using a clamp, the silage produced at the edges of the clamp, i.e. adjacent the walls 17*a-c* in FIG. 3, tends to be of lower nutritional quality relative to the silage produced in the center of the clamp, i.e. away from the walls 17*a-c*. This is because, typically, the portions of the body 18 adjacent the walls 17*a-c* are unable to be compacted to the same degree as portions of the body 18 away from the walls 17*a-c*. As such, if an algorithm of the controller 32 of the system 30 determines that a portion 10*i* is of lower quality based on its one or more characteristics and should be deposited at an edge of the storage space 16, where it might go to waste anyway, the output 37 of the system 30 indicates that the portion is to be deposited in such a location.

Further, where portions 10*i* are of at least acceptable quality, but vary in terms of their moisture and/or nutrient quality, the algorithm may seek to deposit individual portions so as to achieve more homogeneous moisture and/or nutrition across the storage space 16, for example by seeking to place a relatively low moisture or nutrient portion adjacent a relatively high moisture or nutrient portion.

Alternatively, the algorithm may be configured to locate higher nutrient and lower nutrient portions in different locations in the storage space 16. For example, different nutrient levels may be deposited in different locations in the y direction so as to coincide with when lactation periods of cows fed with the silage are anticipated to fall in the consumption of the silage from the front of the space 16 to the rear. Alternatively, different nutrient levels may be deposited in different locations in the x direction, so that if a farmer wishes to feed higher quality silage they may obtain that silage from one side of the storage space 16, or lower quality silage from the opposite side.

The system may be provided with one or more pre-set algorithms that may be selected and/or adjusted by the farmer, or by a contractor, prior to a depositing.

Once the controller 32 determines a location at which the portion 10*i* is to be deposited in the storage space 16, the system 30 produces the output 37 indicative of the determined location. The output 37 may be provided to an operator of the working machine 1 via the output device 39 as previously described, who may then proceed to deposit the portion 10*i* in the indicated location in the storage space 16. As the operator moves the working machine 1 towards the location the output 37 may alter to indicate that the location is approaching or has been reached via audible and/or visual indications such a higher pitch sounds, target indicia on a screen, for example.

In step 108, the controller 32 determines whether the portion 10*i* has been deposited in the storage space 16. The method proceeds to step 110 only when the controller 32 determines that the portion 10*i* has been deposited in the storage space 16.

In step 110, the controller 32 determines the location at which the portion 10*i* is deposited in the storage space 16 based on at least the input from the second device assembly 36.

If an operator ignores the location and deposits the portion 10*i* in a different location, this is still recorded and the algorithm may adapt to seek to maintain its desired strategy for storing the harvested crop over the entire filling operation. The controller may also log when an operator ignores the instructions, so as to provide feedback for operator training.

In step 112, the controller 32 stores the determined one or more characteristics and the determined location of the portion 10*i* in the database 38. The method then proceeds to step 114.

In step 114, the controller 32 determines whether there is another portion of harvested crop 10*i* to be deposited in the storage space 16. For example, the controller 32 may receive a user input indicating whether another portion 10*i* is to be deposited. Alternatively, the controller 32 may determine whether another portion 10*i* to be deposited in the storage space 16 depending on whether the sensor assembly 35 detects that the load handling implement 8 handles another portion 10*i* within a predetermined amount of time starting from the time that the previous portion 10*i* was deposited. If the controller 32 determines that there are no other portions 10*i* to be deposited ('N'), the method terminates. Otherwise, if the controller 32 determines that there is another portion 10*i* to be deposited, the method returns to step 102.

Once the one or more characteristics and the deposition location for each portion 10*i* of the body of the harvested crop 18 has been determined and stored in the database 38, a mapping of the one or more characteristics of the body of the harvested crop 18 can be obtained.

Figure 8:
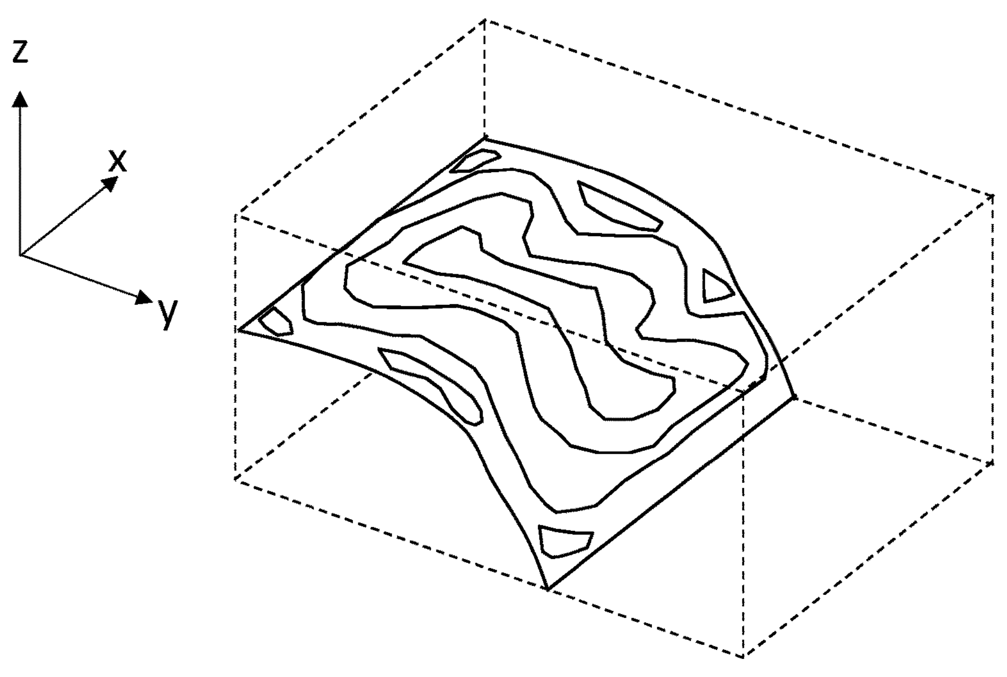
FIG. 8 is an example of a mapping produced from the output of the system of FIG. 5.

As a first example of a mapping produced from the data stored in the database 38, FIG. 8 shows a schematic of a three-dimensional "heat map" shaped to correspond to the top layer of the body 18. For example, the heat map may indicate the values of one of the determined characteristics of the portions 10*i* of the body 18 averaged along the z-direction. Alternatively, the heat map may indicate the values of one of the determined characteristics of the portions 10*i* of the body 18 for a particular layer 24 of the body 18, e.g. the top layer, or averaged values for two or more layers 24 of the body 18.

Figure 9:
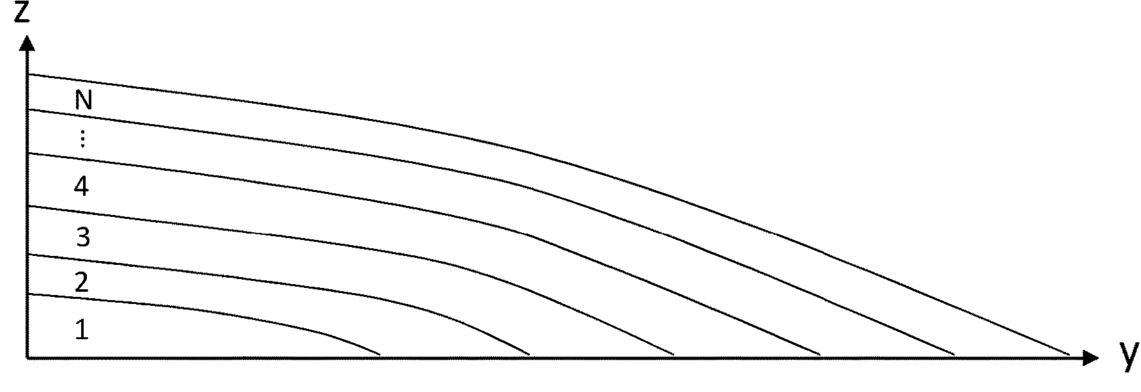
FIG. 9 is an example of a mapping produced from the output of the system of FIG. 5.

As a second example of a mapping produced from the data stored in the database 38, FIG. 9 shows a schematic of a y-z slice through the body 18, the slice including N separate bands. The table shown in FIG. 11 may indicate averaged data for the one or more characteristics of each band such as harvesting location, harvesting time, moisture content, dry matter content and sugar content for example.

Such mappings produced from the data stored in the database 38 may enable a farmer or the like to predict or determine the quality of silage produced from the body 18. This may add a new dimension of knowledge to the farmer when it comes to making feed rationing plans for the winter ahead, based on what is expected, as they have a "map" of their silage clamp to work from. Moreover, such mappings may also enable the farmer to make reactive plans around a following year's crop harvest based on what is found in the clamp once it is consumed during the winter, since the farmer may be able to link low or high quality silage to its production attributes when it was grown, harvested and consolidated in the storage space 16.

Such mappings may also be beneficial if a contractor has been paid by a farmer to form the body 18 since it enables the contractor to provide evidence to the farmer of the quality of the harvested crop 10 forming the body 18 and its variation within the storage space 16.

Figure 10A:
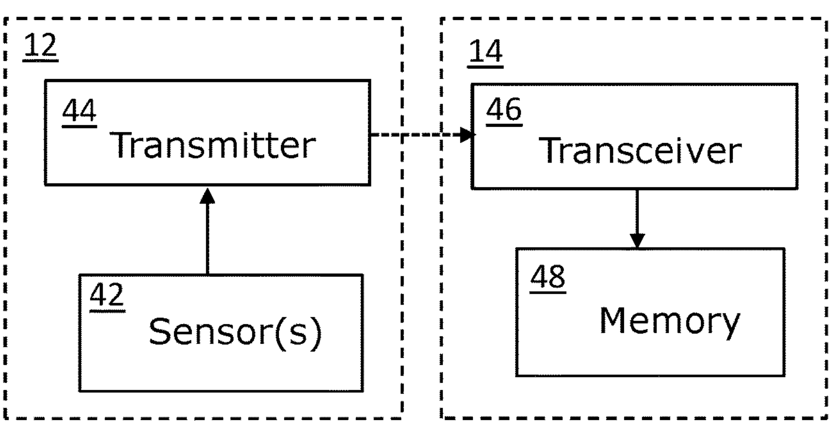
FIGS. 10A and 10B are block diagrams representing communication between a harvesting machine, a harvested crop transport vehicle and a system for mapping one or more characteristics of the body of the harvested crop according to an embodiment of the present teachings.
Figure 10B:
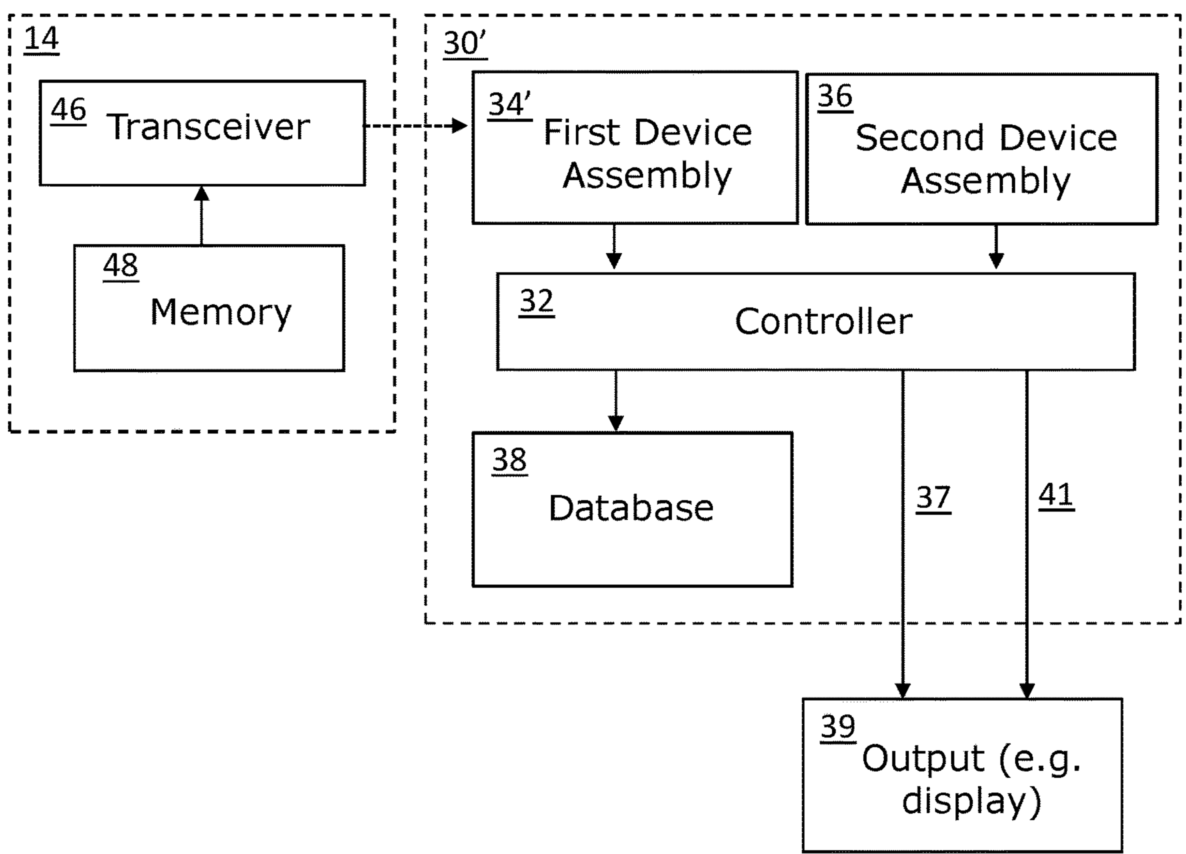
Figure 11:
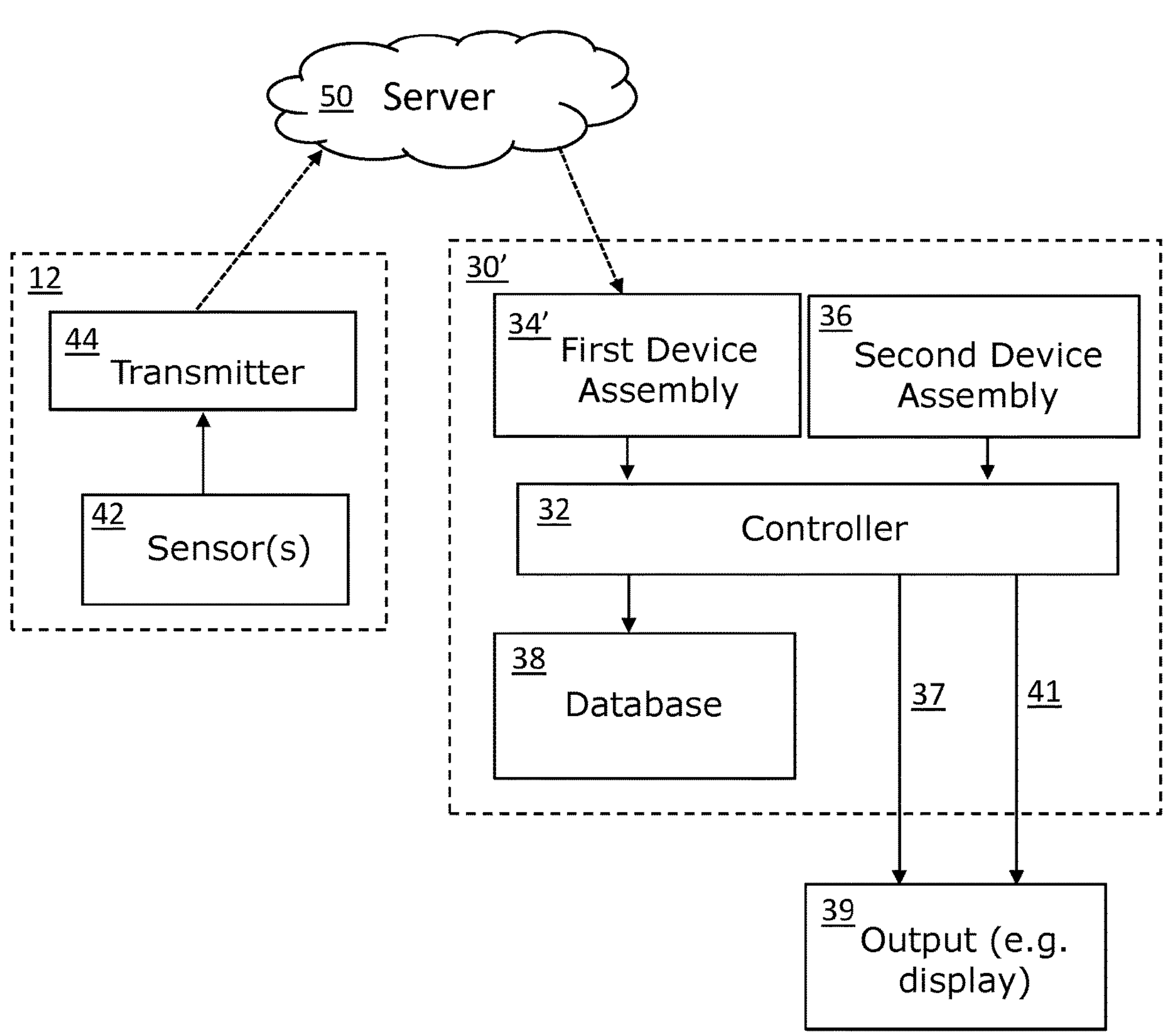
FIG. 11 is a block diagram representing communication between the harvesting machine and the system of FIGS. 10A and 10B according to an embodiment of the present teachings.

With reference to FIGS. 10A-11, an alternative embodiment of a system 30' for mapping one or more characteristics of the body of the harvested crop 18 stored in the storage space 16 will now be described. Features in common with the system 30 of FIG. 5 are denoted with common reference numerals and their description shall not be repeated for brevity. The working machine 1 may include the system 30'.

The system 30' includes the controller 32, the second device assembly 36, and the database 38 of the system 30 of FIG. 5. Moreover, like the system 30 of FIG. 5, the system 30' is configured to produce outputs 37, 41 and provide said outputs 37, 41 to the output device 39.

The system 30' of FIGS. 10A-11 includes an alternative first device assembly 34' to the system 30 of FIG. 5. The first device assembly 34' of the system 30' includes a receiver device configured to receive one or more characteristics of each of the portions 10*i* via wireless communication.

In the illustrated embodiment, the one or more characteristics of each of the portions 10*i* received by the receiver device originates from one or more sensors 42 mounted to the harvesting machine 12. The one or more sensors 42 may include a location sensor (e.g. a global navigation satellite system (GNSS) receiver), and/or one or more of the sensors of the sensor assembly 35 previously described. The location sensor may sense one or more characteristics of each of the portions 10*i*. Such one or more characteristics may include an indication of the harvesting location 13 where each portion 10*i* is harvested, e.g. an indication of the field where each portion 10*i* is harvested, and/or an indication of the specific location within the harvesting location 13 where each portion 10*i* is harvested, e.g. the geographic coordinates of the specific location where each portion 10*i* is harvested.

In alternative embodiments (not shown), the one or more characteristics of each of the portions 10*i* received by the receiver device 34 may originate from one or more sensors mounted to the transport vehicle 14, or from one or more sensors mounted to the harvesting machine 12 and one or more sensors mounted to the transport vehicle 14.

As shown in FIGS. 10A-11, the harvesting machine 12 includes a suitable wireless transmitter device 44 in communication with the one or more sensors 42. The receiver device of the first device assembly 34' receives the one or characteristics of each of the portions 10*i* sensed by the one or more sensors 42 via the transmitter device 44. Transmission may be via a suitable short range wireless protocol such as Bluetooth® or Zigbee® for example.

With reference to FIGS. 10A and 10B, a first example of how the receiver device of the first device assembly 34' may receive the one or characteristics of each of the portions 10*i* sensed by the one or more sensors 42 via the transmitter device 44 will be described.

With reference to FIG. 10A, for each load 11 transferred from the harvesting machine 12 to the transport vehicle 14, the transmitter device 44 is configured to transmit the one or more characteristics of each of the portions 10*i* within said load 11 to a transceiver device 46 mounted to the transport vehicle 14 via wireless communication. The transport vehicle 14 subsequently stores the received one or more characteristics of each of the portions 10*i* in an onboard memory device 48.

The one or more characteristics of the portions 10*i* of the load 11 transmitted to the transceiver device 46 and stored in the memory device 48 may be averaged across all the portions 10*i* of the load 11. This is because it may be difficult to determine where a particular portion of harvested crop 10*i* is located in the transport vehicle 14 after being transferred from the harvesting machine 12, e.g. if the harvested crop is transferred from the harvesting machine 12 to the transport vehicle 14 via blowing as illustrated in FIG. 2A.

Alternatively, the load 11 may be split into two or more sections and the one or more characteristics of the portions 10*i* transmitted to the transceiver device 46 and stored in the memory device 48 may be identical for all of the portions 10*i* forming each section. In such cases, the one or more characteristics stored in the memory device 48 for each section of the load 11 may be averages of the one or more characteristics of all of the portions 10*i* forming each section. For example, the load 11 may be split into a first section located at the front of the transport vehicle 14 and a second section located at the rear of the transport vehicle 14. As such, the memory device 48 also stores section identification information for each section, such as a location of each section with respect to the transport vehicle 14, in the memory device 48. In some embodiments, each section may include one or more portions 10*i*.

The harvesting machine 12 or the transport vehicle 14 may determine which section each of the portions 10*i* transferred from the harvesting machine 12 to the transport vehicle 14 is included in via any suitable means. For example, the determination may be based on the dimensions of the trailer in addition to an azimuthal angle of the spout 12*s* of the harvesting machine 12, and/or a relative position of the transport vehicle 14 relative to the spout 12*s*.

As a further example, the harvesting machine 12 may include a machine vision system configured to determine which section each of the portions 10*i* transferred from the harvesting machine 12 to the transport vehicle 14 is included in. The machine vision system may include a camera which can be aimed at the transport vehicle 14. Based on the images received from said camera, the machine vision system may be able to determine which section each of the portions 10*i* transferred from the harvesting machine 12 to the transport vehicle 14 is included in. Such a machine vision system may be of a type similar to the AUTO FILL system provided by Claas KGaA mbH of Harsewinkel, Germany, but in which the machine vision system is linked to a sensor positioned in the spout 12*s*, and/or to the harvesting location 13 to link the location of the portions 12*i* within the transport vehicle 14 to one or more characteristics of the harvested crop.

As illustrated in FIG. 10B, once the transport vehicle 14 has transported the load 11 from the harvesting location 13 to the vicinity of the storage space 16, the transceiver device 46 transmits the one or characteristics of each of the portions 10*i* of the load 11 stored in the memory device 48, along with the section identification information, if applicable, to the receiver device of the first device assembly 34' via wireless communication. The first device assembly 34' then provides the received one or characteristics of each of the portions 10*i* of the load 11, and the section identification information, if applicable, as characteristics information to the controller 32.

In embodiments in which the load 11 being transported by the transport vehicle 14 is split into two or more sections, the transport vehicle 14 may communicate with the controller 32 such that the controller 32 can determine from which section a portion 10*i* being handled by the working machine 1 belongs, and thus the one or more characteristics of that portion 10*i* received via the receiver device 40.

With reference to FIG. 11, a second example of how the receiver device of the first device assembly 34' may receive the one or characteristics of each of the portions 10*i* sensed by the one or more sensors 42 via the transmitter device 44 will be described.

In FIG. 11, the transmitter device 44 on the harvesting machine 12 transmits the one or more characteristics of each of the portions 10*i* within a given load 11 sensed by the one or more sensors 42, along with the section identification information, if applicable, to a remote server 50 via wireless communication (e.g. via a suitable cellular wireless communication protocol such as GPRS, UMTS, HSPA, 5G etc.). The receiver device of the first device assembly 34' subsequently receives the one or characteristics of each of the portions 10*i* within said load 11 and the section identification information, if applicable, from the remote server 50 via wireless communication. The first device assembly 34' then provides the received one or characteristics of each of the portions 10*i* of the load 11 and the section identification information, if applicable, as characteristics information to the controller 32.

In instances where more than one transport vehicle 14 is used to transport a load of a harvested crop 11 from the harvesting machine 12 to the storage space 16, the transmitter device 44 may transmit a transport vehicle ID to the server 50, which associates a particular load 11 with a particular transport vehicle 14. The receiver device 40 may then receive the transport vehicle ID for each load 11. As such, when a particular transport vehicle 14 arrives at the storage space 16, the system 30 can determine the characteristics information of the load 11 being transported by that transport vehicle 14. Alternatively, the remote server 50 may track the location of each load 11, for example via a global navigation sensor system (GNSS) receiver mounted to the transport vehicle 14, and send the one or more characteristics and section identification information, if applicable, for said load 11 to the receiver device 40 when the transport vehicle 14 transporting the load 11 arrives at the vicinity of the storage space 16.

In a further example (not shown), the receiver device of the first device assembly 34' may receive the one or more characteristics of each of the portions 10*i* sensed by the one or more sensors 42 via direct wireless communication with the transmitter 44 of the harvesting machine 12.

In an alternative embodiment (not shown), the first device assembly 34' of the system 30' may further include the sensor assembly 35 of the system 30. In such an embodiment, certain parameters may be determined from a sensor 42 located on the harvesting machine 12 and other parameters may be sensed at the attachment 7 of the working machine 1.

In the foregoing description, the working machine 1 includes the system 30, 30'. In alternative embodiments (not shown), the system 30, 30' may be partially or wholly separate from the working machine 1. In such embodiments, one or more of the first device assembly, the second device assembly, the controller, and the database may be located remotely from the working machine 1. For example, the receiver device, the controller, and the database may be located remote from the working machine 1 in a fixed position in the vicinity of the storage space 16, or in a cloud-based computing system. For example, the remote server 50 of FIG. 11 may include one or more of the receiver device, the controller, and the database. The second device assembly may also be located remote from the working machine 1. For example, the second device assembly may include one or more cameras fixed relative to the storage space 16 and with a field of view including the storage space 16, and the controller may determine the location at which each of the portions 10*i* is deposited in the storage space 16 from said one or more cameras. Components of the system that are remote from the working machine 1 may communicate with components of the working machine 1, for example the output device 39, via wireless communication.

Although the embodiments described above utilize an operator driving the working machine and following instructions from the controller, in other embodiments, the depositing of the harvested crop may instead be carried out in an automated process based on the outputs of the algorithm. For example, the working machine may be an autonomous vehicle whose movements and working operations are directly controlled by the controller. Alternatively, the harvested crop may instead be deposited in the body by other means, such as being blown or conveyed on a moveable conveying device, the position of which is controlled by the controller.

The invention claimed is:

1. A system for mapping one or more characteristics of a body of a harvested crop stored in a storage space for forming a single contiguous body of harvested crop, the system comprising:

a controller;

a first device assembly providing an input to the controller; and a second device assembly providing an input to the controller, wherein the controller is configured to determine one or more characteristics respectively of each of a plurality of portions of the body of the harvested crop, the one or more characteristics comprising one or more of dry matter content, moisture content, level of contamination, and/or one or more nutrient values, prior to the deposition of each of said portions in the storage space, based on at least the input from the first device assembly, wherein the controller is configured to determine a respective location within the storage space at which location each of said portions is deposited in the storage space based on at least the input from the second device assembly, wherein the controller is configured to store the respective determined one or more characteristics and the respective determined location of each of said portions in a database, and wherein the controller is configured to determine the location for depositing one or more additional portions of the body of the harvested crop within the storage space based on the one or more determined characteristics of one or more previously deposited portions of the body of the harvested crop to achieve a desired distribution of characteristics within the single contiguous body of harvested crop in the storage space.

2. The system of claim 1, further configured to produce an output indicative of a location at which one or more of said portions is to be deposited in the storage space based on the determined one or more characteristics of said one or more portions.

3. The system of claim 2, further configured to produce an output indicating that a portion of a harvested crop is to be deposited separately from the storage space based on one or more characteristics of said portion determined by the controller based on at least the input from the first device assembly.

4. The system of claim 1, wherein the second device assembly is configured to determine the location at which each of said portions is deposited in the storage space in at least one of an x-direction, a y-direction, and/or a z-direction.

5. The system of claim 4, wherein the second device assembly includes at least one of: a GNSS receiver, an inertial sensor, a tilt sensor, a steering angle sensor, and a travelling speed sensor, a LIDAR sensor, an electronic compass, and a camera.

6. The system of claim 1, wherein the input provided by the first device assembly to the controller corresponds to characteristics information originating from one or more sensors configured to sense the one or more characteristics of each of said portions.

7. The system of claim 6, wherein the first device assembly comprises a receiver device configured to receive the characteristics information via wireless communication.

8. The system of claim 7, wherein the receiver device is configured to receive the characteristics information via wireless communication with a harvested crop transport vehicle, a harvesting machine, and/or a remote server.

9. The system of claim 6, wherein the first device assembly comprises a sensor assembly configured to sense one or more characteristics of each of said portions to determine the characteristics information, and wherein the sensor assembly includes at least one of: a nutrient sensor for sensing one or more nutrient values of a harvested crop, a moisture content sensor for sensing a moisture content of a harvested crop, a dry matter content sensor for sensing a dry matter content of a harvested crop, and/or a contamination sensor for sensing a level of contamination of a harvested crop.

10. The system of claim 1, wherein the plurality of portions are deposited to form a plurality of layers within the body of the harvested crop, and wherein the controller is further configured to store the determined one or more characteristics and the determined location for each of said plurality of layers in the database.

11. A working machine comprising a system for mapping one or more characteristics of a body of a harvested crop stored in a storage space for forming a single contiguous body of harvested crop, the system comprising:

a controller;

a first device assembly providing an input to the controller;

a second device assembly providing an input to the controller, wherein the controller is configured to determine one or more characteristics respectively of each of a plurality of portions of the body of the harvested crop, the one or more characteristics comprising one or more of dry matter content, moisture content, level of contamination, and/or one or more nutrient values, prior to the deposition of each of said portions in the storage space, based on at least the input from the first device assembly; and a load handling apparatus for handling the plurality of portions of the body of the harvested crop and depositing each of the plurality of portions of the body of the harvested crop in the storage space, wherein the controller is configured to determine a respective location within the storage space at which location each of said portions is deposited in the storage space based on at least the input from the second device assembly, wherein the controller is configured to store the respective determined one or more characteristics and the respective determined location of each of said portions in a database, wherein the controller is configured to determine the location for depositing one or more additional portions of the body of the harvested crop within the storage space based on the one or more determined characteristics of one or more previously deposited portions of body of the harvested crop to achieve a desired distribution of characteristics within the single contiguous body of harvested crop in the storage space, and wherein the working machine further comprises:

a ground engaging structure for moving over the body of the harvested crop.

12. The working machine of claim 11, wherein the input provided by the first device assembly to the controller corresponds to characteristics information originating from one or more sensors configured to sense the one or more characteristics of each of said portions, wherein the first device assembly comprises a sensor assembly configured to sense one or more characteristics of each of said portions to determine the characteristics information, and wherein the sensor assembly includes at least one sensor mounted to the load handling apparatus and configured to sense one or more characteristics of a portion of a harvested crop being handled by the load handling apparatus.

13. The working machine claim 11, further comprising a weight sensor configured to determine a weight of a portion of a harvested crop being handled by the load handling apparatus, the weight sensor providing an input to the controller, and/or further comprising a volume sensor configured to determine a volume of a portion of a harvested crop being handled by the load handling apparatus, the volume sensor providing an input to the controller.

14. A computer implemented method for mapping one or more characteristics of a body of a harvested crop stored in a storage space for forming a single contiguous body of harvested crop, the method comprising:

(a) determining, via a first device assembly, one or more characteristics respectively of each of a plurality of portions of the body of the harvested crop, the one or more characteristics comprising one or more of dry matter content, moisture content, level of contamination, and/or one or more nutrient values, prior to the deposition of each of said portions in the storage space;

(b) determining, via a second device assembly, a respective location within the storage space at which location each of said portions is deposited in the storage space; and (c) storing, in a database, the respective determined one or more characteristics and the respective determined location of each of said portions, wherein the controller is configured to determine the location for depositing one or more additional portions of the body of the harvested crop within the storage space based on the one or more determined characteristics of one or more previously deposited portions of body of the harvested crop to achieve a desired distribution of characteristics within the single contiguous body of harvested crop in the storage space.

15. The method of claim 14, further comprising:

producing an output indicative of a location at which one or more of said portions is to be deposited in the storage space based on the determined one or more characteristics of said one or more portions; and/or producing an output indicating that a portion of a harvested crop is to be deposited separately from the storage space based on one or more characteristics of said portion determined via the first device assembly.

16. The method of claim 14, wherein in step (a), the one or more characteristics of each of said portions is determined, via the first device assembly, from characteristics information originating from one or more sensors configured to sense the one or more characteristics of each of said portions.

17. The method of claim 16, wherein the first device assembly comprises a receiver device, and wherein step (a) further comprises:

the receiver device receiving the characteristics information via wireless communication; and wherein the receiver device receives the characteristics information via wireless communication with a harvested crop transport vehicle, a harvesting machine, and/or a remote server.

18. The method of claim 16, wherein the first device assembly comprises a sensor assembly and wherein step (a) further comprises:

sensing, via the sensor assembly, one or more characteristics of each of said portions to determine the characteristics information.

19. The method of claim 14 performed by a working machine comprising:

the first device assembly;

the second device assembly;

a ground engaging structure for moving over the body of the harvested crop; and a load handling apparatus for handling the plurality of portions of the body of the harvested crop and depositing each of the plurality of portions in the storage space.

* * * * *